US009717798B2

(12) United States Patent
Haddad et al.

(10) Patent No.: US 9,717,798 B2
(45) Date of Patent: Aug. 1, 2017

(54) POLYMERIC COLORANT COMPOSITIONS AND METHODS OF USE

(71) Applicant: 3M INNOVATIVE PROPERTIES COMPANY, St. Paul, MN (US)

(72) Inventors: Louis C. Haddad, Mendota Heights, MN (US); Douglas A. Hanggi, Woodbury, MN (US); David B. Olson, Marine on St. Croix, MN (US); Matthew T. Scholz, Woodbury, MN (US); Dong-Wei Zhu, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/358,817

(22) PCT Filed: Nov. 16, 2012

(86) PCT No.: PCT/US2012/065404
§ 371 (c)(1),
(2) Date: May 16, 2014

(87) PCT Pub. No.: WO2013/074860
PCT Pub. Date: May 23, 2013

(65) Prior Publication Data
US 2014/0323578 A1    Oct. 30, 2014

Related U.S. Application Data

(60) Provisional application No. 61/560,407, filed on Nov. 16, 2011.

(51) Int. Cl.
| A61K 47/34 | (2017.01) |
| A61K 31/167 | (2006.01) |
| A61K 47/32 | (2006.01) |
| A61K 31/4425 | (2006.01) |
| A61K 31/155 | (2006.01) |
| A61K 47/44 | (2017.01) |
| A61K 9/00 | (2006.01) |
| A61K 9/107 | (2006.01) |
| A01N 43/40 | (2006.01) |
| A01N 47/44 | (2006.01) |

(52) U.S. Cl.
CPC .............. *A61K 47/34* (2013.01); *A01N 43/40* (2013.01); *A01N 47/44* (2013.01); *A61K 9/0014* (2013.01); *A61K 9/107* (2013.01); *A61K 31/155* (2013.01); *A61K 31/167* (2013.01); *A61K 31/4425* (2013.01); *A61K 47/32* (2013.01)

(58) Field of Classification Search
CPC ...... A01N 43/40; A01N 47/44; A61K 31/155; A61K 31/167; A61K 31/4425; A61K 47/32; A61K 47/34; A61K 9/0014; A61K 9/107
See application file for complete search history.

(56) References Cited

U.S. PATENT DOCUMENTS

| 3,337,288 A | * | 8/1967 | Horiguchi | C08F 4/00 430/108.1 |
| 4,051,138 A | * | 9/1977 | Wang | A61K 8/817 524/106 |
| 4,542,012 A | | 9/1985 | Dell | |
| 4,584,192 A | | 4/1986 | Dell | |
| 5,435,660 A | | 7/1995 | Wirt | |
| 5,547,662 A | | 8/1996 | Khan | |
| 5,643,907 A | * | 7/1997 | Swirska | A61K 31/535 514/236.8 |
| 6,248,085 B1 | | 6/2001 | Scholz | |
| 6,422,778 B2 | | 7/2002 | Baumann | |
| 6,605,666 B1 | | 8/2003 | Scholz | |
| 6,672,704 B2 | | 1/2004 | Katakura | |
| 6,838,078 B2 | | 1/2005 | Wang | |
| 6,930,184 B2 | | 8/2005 | Olson | |
| 7,030,203 B2 | | 4/2006 | Mosbey | |
| 7,147,873 B2 | | 12/2006 | Scholz | |
| 7,261,701 B2 | | 8/2007 | Davis | |
| 7,377,710 B2 | | 5/2008 | Baumann | |
| 7,459,167 B1 | | 12/2008 | Sengupta | |
| 2004/0105826 A1 | * | 6/2004 | Soane | A61K 8/11 424/59 |
| 2004/0202625 A1 | * | 10/2004 | Daniloff | A61L 31/14 424/63 |

(Continued)

FOREIGN PATENT DOCUMENTS

| CN | 101175404 | 5/2008 |
| EP | 1489144 | 12/2004 |

(Continued)

OTHER PUBLICATIONS

Dahl, "Pure Singlet Oxygen Cytotoxicity for Bacteria", Photochemistry and Photobiology, 1987, vol. 46, No. 3, pp. 345-352.
International Search Report for PCT International Application No. PCT/US2012/065404 mailed on Apr. 9, 2013, 4 pages.
Wang, et al., Applications of Functional Macromolecular Colorants in Hi-technology, etc., Advances in Fine Petrochemicals, vol. 5, No. 9, pp. 39-42 and 50, Sep. 30, 2004.

*Primary Examiner* — Aradhana Sasan

(57) ABSTRACT

A composition is disclosed. The composition comprises at least one polymeric colorant having a polymer component with a colorant component covalently bound thereto, a medicament, and a liquid vehicle. The at least one colorant component does not react directly or indirectly with the medicament. Methods of using the polymeric colorants, including a method for the preparation of skin as a site for a surgical procedure and a method of treating a medical condition, are also provided.

22 Claims, No Drawings

(56) References Cited

U.S. PATENT DOCUMENTS

| | | |
|---|---|---|
| 2005/0058673 A1 | 3/2005 | Scholz |
| 2006/0051384 A1 | 3/2006 | Scholz |
| 2006/0051385 A1 | 3/2006 | Scholz |
| 2006/0074021 A1 | 4/2006 | Mor |

FOREIGN PATENT DOCUMENTS

| | | |
|---|---|---|
| WO | WO 00-78854 | 12/2000 |
| WO | WO 01-17356 | 3/2001 |
| WO | WO 02-04034 | 1/2002 |
| WO | WO 2004-083905 | 9/2004 |
| WO | WO 2008-057773 | 5/2008 |
| WO | WO 2009-088894 | 7/2009 |
| WO | WO 2009-089346 | 7/2009 |
| WO | WO 2010-079025 | 7/2010 |

* cited by examiner

POLYMERIC COLORANT COMPOSITIONS AND METHODS OF USE

CROSS REFERENCE TO RELATED APPLICATIONS

This application is a national stage filing under 35 U.S.C. 371 of PCT/US2012/065404, filed Nov. 16, 2012, which claims priority to U.S. application No. 61/560,407, filed Nov. 16, 2011, the disclosure of which is incorporated by reference in its/their entirety herein.

BACKGROUND

Applicators for applying liquids such as medicaments or cleansing agents are known in the art. Conventional applicators typically provide a generally cylindrical body construction and include a glass ampoule retained within the body, the ampoule containing a liquid comprising the medicament or cleansing agent; a sponge or tip secured to the body, at least one surface of which is in fluid communication with the ampoule; and a means for fracturing the ampoule such that when the ampoule is fractured, the liquid stored therein is dispensed to the sponge for application.

When a non-colored or clear liquid is applied using these applicators, it is difficult for the user to see where the liquid has been applied. Thus, in many situations, it is necessary to utilize colored liquid so that the user knows where the liquid has been applied. For example, antiseptics or medicaments used as a pre-operative liquid are applied to the body just prior to surgery. It is beneficial that the user be able to see where the pre-operative liquid has been applied. If the pre-operative liquid is colored, it is easier for the user to discern where the liquid has been applied to the body.

A surgical site preparation composition including a fugitive solvent, an antimicrobial agent soluble in said solvent, a film-forming material soluble in said solvent, and a dye has been reported. The composition provides a color indication of the skin surface covered by the composition.

In addition, several problems associated with compounding and storing a mixture comprising a liquid medicament or cleansing solution with a color, such as a tint or a dye, have been recognized. Consequently, an applicator configured to contact a non-colored or clear liquid with a porous element containing a colorant as the liquid is transferred from an ampoule to a body has been described.

In spite of these advancements, there remains a need for improved medicament compositions and methods of applying them to a well-defined portion of a body.

SUMMARY

In general, the present disclosure relates to compositions and methods for applying a colored medicament composition to a skin surface. In some embodiments, the compositions and methods of the present disclosure permit precise control of the area to which the composition is applied by providing the operator with a visual (e.g., colored and/or fluorescent) indication of the area to which the composition has been applied. Advantageously, the present disclosure includes a broad range of potential biocompatible colorants, making it possible to formulate medicament compositions that can be applied to and visually observed on any skin surface.

In one aspect, the present disclosure provides a composition. The composition can comprise at least one polymeric colorant comprising a polymeric component with at least one colorant component covalently bound thereto, a medicament, and a liquid vehicle. The at least one colorant component does not react directly or indirectly with the medicament.

In another aspect, the present disclosure provides a composition. The composition can comprise a first polymeric colorant comprising a first polymer component with a first colorant component bound thereto, a second polymeric colorant comprising a second polymer component with a second colorant component covalently bound thereto, a medicament, and a liquid vehicle. Each of the first and second colorant components does not react directly or indirectly with the medicament.

In any of the above embodiments, at least one colorant component can comprise one or more chromophore and/or one or more fluorophore. In any of the above embodiments, at least one polymer component can comprise a natural polymer, a synthetic polymer, a derivative of any of the foregoing polymers, or a mixture of any two or more of the foregoing polymers. In any of the above embodiments, at least one polymer component can be derived from vinyl monomers. In any of the embodiments, at least one polymer component can comprise a condensation polymer. In any of the embodiments, at least one polymer component can comprise a polyamine or a polyamide. In any of the above embodiments, at least one polymeric colorant can comprise a film-forming polymeric colorant. In any of the above embodiments, the composition further can comprise a film-forming polymer. In any of the above embodiments, at least one polymeric colorant can be water-soluble or water-dispersible. In any of the embodiments, at least one polymeric colorant can be water-insoluble. In any of the embodiments, the polymeric colorant can serve as an emulsifier in a water-in-oil emulsion or an oil-in-water emulsion. In any of the above embodiments, at least one colorant component can comprise a dye.

In any of the above embodiments, the medicament can be selected from the group consisting of an antimicrobial agent, an antiseptic, an antibiotic, an analgesic, an enzyme, and a mixture of any of two or more of the foregoing medicaments. In some embodiments, the medicament can comprise an antimicrobial agent and, when the composition is contacted for a period of time with an area of a surface having a number of cultivable microorganisms present thereon, the concentration of antimicrobial compound in the liquid vehicle is sufficient to reduce the number of cultivable microorganisms on the area of the surface. In any embodiment, the composition can comprise a chemical antiseptic compound; an antiseptic alcohol; a cationic antiseptic compound; chlorhexidine, polyhexamethylene biguanide, octenidine, or salts thereof; polyhexamethylene biguanide, octenidine, or a salt of any of the foregoing polycationic compounds.

In any of the above embodiments, the liquid vehicle can comprise water. In any of the above embodiments, the liquid vehicle further can comprise acetone or an alcohol. In any of the above embodiments, the composition further can comprise a foaming agent. In any of the above embodiments, when the composition is applied as a layer onto a predetermined area of a skin surface, the layer formed by an effective amount of the composition can be transparent or translucent.

In another aspect, the present disclosure provides a method of preparing skin as a site for a surgical procedure. The method can comprise providing a composition that includes at least one polymeric colorant comprising a polymer component with a colorant component covalently bound thereto, an antimicrobial agent, and a liquid vehicle; applying the composition to an area of skin selected for the surgical procedure; and verifying the area to which the composition was applied by observing on the skin a color associated with the composition. The antimicrobial agent is present at a sufficient concentration in the composition such that, when a predetermined quantity of the composition is contacted with a predetermined area of skin having a number of cultivable microorganisms present thereon, the antimicrobial agent is capable of reducing the number of cultivable microorganisms.

In another aspect, the present disclosure provides a method of treating a medical condition. The method can comprise providing a composition that includes at least one polymeric colorant comprising a polymer component with a colorant component covalently bound thereto, a medicament, and a liquid vehicle; applying the composition to an area; and verifying the area to which the composition was applied by observing on the area a color associated with the composition. The medicament comprises an active agent in a quantity sufficient to elicit a preselected biological response other than reducing the number of cultivable microorganisms on skin. In some embodiments, the medical condition can be a skin condition. In some embodiments, the preselected biological response can be substantially localized at the area.

In any embodiment of the above methods, observing on the area can comprise observing by using an unaided human eye. In any embodiment of the above methods, the method further can comprise, after applying the composition to the area, allowing a portion of the liquid vehicle to evaporate or be absorbed, wherein verifying the area to which the composition was applied by observing a color associated with the composition is performed after the portion of the liquid vehicle is allowed to evaporate or be absorbed.

In any embodiment of the above methods, wherein applying the composition can comprise applying a layer of the composition; wherein, after applying an effective amount of the composition onto the treatment area and, optionally, allowing a portion of the liquid vehicle to evaporate or be absorbed, the layer is transparent or translucent. In any embodiment of the above methods, the method further can comprise visually observing a marking or an anatomical feature through the composition after the composition is applied to the area and, optionally, a portion of the liquid vehicle is allowed to evaporate or be absorbed. In any embodiment of the above methods, the method further can comprise performing a surgical procedure. The surgical procedure can comprise making an incision, performing a percutaneous injection, or performing a percutaneous insertion of a medical device. In any embodiment of the above methods, applying the composition to the skin site can comprise applying the composition in the form of an aerosol or foam. In any embodiment of the above methods, the method further can comprise removing the composition from the area to which it is applied.

In another aspect, the present disclosure provides a method of killing microorganisms on mammalian skin prior to a percutaneous procedure. The method can comprise providing a composition that includes at least one polymeric colorant comprising a polymer component with a colorant component covalently bound thereto, an antimicrobial, and a liquid vehicle; applying the composition to an area of mammalian skin; and verifying, by human eye, the area to which the composition was applied by observing on the area a color associated with the composition. The antimicrobial is present in a concentration of at least 0.25% wt/wt of the composition. Applying the composition to the area reduces the number of cultivable microorganisms on the mammalian skin.

In another aspect, the present disclosure provides a kit. The kit can comprise a sealed container containing a composition that includes a medicament, a liquid vehicle, and at least one polymeric colorant comprising a polymer component with a colorant component covalently bound thereto. The at least one colorant component does not react directly or indirectly with the medicament. In any embodiment of the kit, the at least one colorant component can comprise one or more chromophore and/or one or more fluorophore. In any of the above embodiments, the kit further can comprise an applicator for applying the composition to skin. The applicator can be adapted to be operationally coupled to at least one of the sealed containers.

In any embodiment of the kit, the medicament can comprise an antimicrobial agent. When the composition is contacted for a period of time with an area of a surface having a number of cultivable microorganisms present thereon, the concentration of antimicrobial agent in the liquid vehicle is sufficient to reduce the number of cultivable microorganisms in the area.

In any of the above embodiments of the kit, the kit further can comprise a plurality of sealed containers, each of the plurality of containers containing the composition. In any of the above embodiments of the kit, the kit further can comprise a rinse solution. In some embodiments, the rinse solution can comprise an agent that counteracts an activity of the medicament.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Colorant component", as used herein, refers to any chemical group capable of selective light absorption and or fluorescence, thereby enabling optical detection (e.g., by a human eye). Colorant components molecules can act as a chromophore, a fluorophore, or both. A chromophore can selectively absorb light, imparting coloration to a polymer to which it is bound. A fluorophore selectively absorbs light of a first wavelength and emits light at a second wavelength, imparting fluorescence to a polymer to which it is bound.

"Visible" and "optical indication", as used herein, refers to colorants used according to the present disclosure wherein a composition comprising the colorant has a color that is visible to a human eye when the composition is illuminated with wavelengths of light in the visible or ultraviolet portions of the electromagnetic spectrum.

"Condensation polymer", as used herein, refers to any kind of polymer formed through a condensation reaction, releasing small molecules (e.g., water, methanol) as by-products of the condensation. Examples of condensation polymers include, for example, polyamides, polyacetals, and polyesters.

"Lower alcohol", as described herein, refers to an alcohol comprising one to four carbon atoms and a single hydroxyl group. Nonlimiting examples of lower alcohols include methyl alcohol, ethyl alcohol, n-propyl alcohol, isopropyl alcohol, and butyl alcohol.

"Medicament", as used herein, refers to an agent eliciting a desired and clinically-therapeutic local and/or systemic biological response when the composition contacts skin or a mucous membrane. Nonlimiting examples of medicaments include an antimicrobial agent, an antiseptic, an antibiotic, an analgesic, a thrombolytic agent, a fibrinolytic agent, a local anesthetic, an anti-inflammatory including both steroidal and nonsteroidal anti-inflammatories, an enzyme, and a mixture of any of two or more of the foregoing. Preferred medicaments are antiseptic agents effective against bacteria and fungi, i.e. capable of killing bacteria and/or fungi present on mammalian tissue (e.g. skin and/or mucosal tissue).

"Biological response", as used herein, refers to a specific physiological change that occurs in a cell, tissue, organ, and/or organism in response to contact with a medicament. In some instances, the particular biological response by certain cells, tissue, organs or organisms may be specific to a particular medicament. In some instances, a particular biological response may be common to a group or class of medicaments. Nonlimiting examples of particular biological responses include cell death and/or the inhibition of cell proliferation in response to contact with an antimicrobial agent. The biological response may relate specifically to the killing or inactivation of microorganisms. For certain medicaments applied to mammalian tissue the biological response is typically a local tissue response.

"Normal skin flora" refers to resident skin flora present on the skin of a healthy person and often consists predominantly of *Staphylococcus epidermidis*. Normal skin flora does not relate to seeded flora which is artificially applied to skin.

"Polymer" includes homopolymers and copolymers of any length (including oligomers) and "copolymer" includes a polymer of two or more types of polymerizable monomers, and therefore includes terpolymers, tetrapolymers, etc., which can include random copolymers, block copolymers, or sequential copolymers.

"Film-forming", as used herein, refers to polymers and compositions which can be dried to leave a cohesive and continuous covering over the hair or skin when applied to their surface. Preferred film formers are pliable and can be flexed on the skin without cracking.

"Photodynamic effect", as used herein, is used to describe destruction of cells and microbes by reactive oxygen species (e.g., singlet oxygen, hydroxyl radical, and superoxide radical anion) that are generated by photosensitizer dyes (e.g., triplet-sensitizers such as rose bengal, for example) in the presence of light and oxygen. The effect is described, for example, in Dahl et al., *Photochemistry and Photobiology*, 46:345-352 (1987).

"Polymer component", as used herein, specifically refers to the polymeric backbone of a polymeric colorant molecule. The polymer component may optionally include noncolorant pendant groups that do not substantially interfere with the function of the colorant component or the medicament. It is recognized that, in some embodiments, the composition further may comprise other polymer molecules that do not have a chromophore or a fluorophore bound thereto.

"Polymeric colorant", as used herein, refers to a molecule having a polymer component with at least one colorant component (e.g., at least one chromophore and/or at least one fluorophore) bound thereto. Polymeric colorant molecules are sufficiently large enough and/or have polar groups such that the molecules do not freely diffuse through a cell membrane. The colorant component may be present as part of the polymeric colorant backbone (e.g. part of the main chain) or it may be present in pendant positions or both. Preferred polymeric colorants have a number average molecular weight of at least 1000 daltons, preferably at least 2000 daltons and most preferably at least 5000 daltons. Polymeric colorants may be cationic, anionic, nonionic or zwitterionic. Preferred polymeric colorants for skin and mucosal tissue are positively charged or nonionic.

"Substantive" as it applies to a composition (or a film-forming polymer) means that when a composition (or a film-forming polymer in solution) is applied to human skin as a uniform wet film in an amount of approximately 4 milligram per square centimeter clean dry skin on an inner forearm and allowed to thoroughly dry (e.g., at least 10 minutes at 23° C. and 50% relative humidity), it resists removal under running tap water at a temperature of about 23° C. to about 24° C. and a flow rate of about 2.4-2.5 liters/minute (L/min) falling from a height of 15 centimeters (cm) and striking the skin immediately above the dry composition (not directly on the dry composition) and then flowing over the dry composition for at least about 15 seconds.

"Liquid vehicle", as used herein, refers to a volatile liquid in which the polymeric colorants of the present disclosure are dissolved, dispersed, and/or suspended. Water (e.g., sterile water or water-for-injection), ethanol/water solutions having 60-95% ethanol, isopropanol/water solutions having 65-95% isopropanol are nonlimiting examples of liquid vehicles.

"Bound to a polymer" or "polymer-bound" refers to a group (e.g., a colorant component) that is attached to a polymer through covalent bonds under ambient use and/or storage conditions. For example, a heterocyclic ring or a substituent thereof may be polymer-bound via covalent attachment of the heterocyclic ring or substituent either through a backbone atom of the polymer, a side chain atom or the polymer, or a terminal atom of the polymer chain.

The term "limits the presence of a virus, a fungus or a bacterium" as used herein refers to methods that employ the use of compositions of the present disclosure (e.g., compositions wherein the medicament comprises an antimicrobial agent) to inhibit, kill, or prevent the replication of or reduce the number of viruses, bacteria or fungi present on a surface (e.g., skin or mucosal tissue) in contact with the composition. Preferably, the term refers to an at least about 40% reduction (as evidenced by the inhibition of growth or killing, for example) in the amount of at least one species of fungus or bacterium detected on a surface under the same conditions using a standardized test method for determining antimicrobial activity (e.g., ASTM E1173-01(2009) Standard Test Method for Evaluation of Preoperative, Precatheterization, or Preinjection Skin Preparations), for a composition of the present disclosure relative to similar compositions that do not include an antimicrobial medicament. More preferably, the compositions of the present disclosure provide at least about 75% reduction, even more preferably, at least about 90% reduction, and most preferably, at least about 99% reduction in the normal skin flora when tested on a "dry site" such as the abdomen relative to similar compositions that do not include an antimicrobial medicament under the same conditions.

The terms "comprises" and variations thereof do not have a limiting meaning where these terms appear in the description and claims.

As used herein, "a," "an," "the," "at least one," and "one or more" are used interchangeably. Thus, for example, a polymeric colorant can be interpreted to mean "one or more" polymeric colorants.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the description below. Other features, objects and advantages will become apparent from the description and from the claims.

DETAILED DESCRIPTION

The present disclosure generally relates to compositions and methods for treating a skin surface. In particular, the compositions include a medicament that exerts a systemic and/or a localized biological effect. Advantageously, the present disclosure provides a composition comprising a colorant that permits more precise control of the area to which the composition is applied. Even more advantageously, the colorant is provided in a form that enables a broad spectrum of colors, making it useful for a wide variety of skin colors. Moreover, the polymeric nature of the colorant advantageously minimizes the potential for absorption of the colorant into the cells and/or dissemination of the colorant into remote tissue of the treated organism.

While applying a composition to a skin site (e.g., for skin disinfection prior to surgery or other invasive processes), it is highly desirable to use a composition that permits visual confirmation of the area to which the composition has been applied. It is particular important to know the application area when applying skin antiseptics such as presurgical skin antiseptics. In addition, most antiseptics contain one or more volatile components which evaporate after application. Thus, it is also desirable for the antiseptic composition to remain visible after drying. Preferably, the dried antiseptic should be highly colored, so the surgical team knows where the skin has been decontaminated. An effective means for visually confirming an applied composition is the inclusion of a visibly-colored reagent that absorbs selected wavelengths of light and, thereby, changes the color of the skin surface to which the composition is applied. Unlike the previous generation of iodine-based antimicrobial preparations, many of the current antimicrobial formulations (e.g., formulations comprising biguanides such as chlorhexidine salts including chlorhexidine gluconate (CHG) and alexidine salts such as alexidine dihydrochloride or other cationic reagents including polyhexamethylene biguanide (PHMB), octinedine, cetyl pyridinium halides, or benzalkonium halides (BA)) are not inherently colored. These formulations require the addition of a colorant compound in order to provide an easily-visible indication of the area to which the formulation is applied. Advantageously, a colored liquid may also help the clinician to apply a uniform coating of antiseptic and avoid unobserved drips which could, in some cases, result in pooling against the skin and thereby potentially causing undesirable effects (e.g., chemical burns).

Presently, the number of colorant compounds approved for use in topical medicament applications is quite limited and varies by government and/or regulatory jurisdiction, such that no globally-acceptable colored topical composition exists. Development of new dyes and colorants can be extremely expensive. Colorant (e.g., dye) species acceptable for such applications within the United States are currently limited to several FD&C dyes that primarily include polyanionic chromophores. Polyanionic compounds (e.g., chromophores), however, exhibit an undesirable tendency to cause useful antimicrobial agents (e.g., cationic antimicrobial agents such as CHG) to precipitate out of an aqueous and/or hydroalcoholic solution. Furthermore, the solubility of these dyes in hydrophobic compositions can also be very limited. An ideal colorant or dye for use in compositions applied to skin is non-toxic, is nonreactive with a medicament (e.g., antiseptic) or any other component in the composition either directly or indirectly (e.g. generating singlet oxygen which can oxidatively degrade the medicament), and is highly colored in the medicament composition when the composition is in both the liquid and dry states.

Many polymeric materials are not typically transported across cell membranes into the cells. Thus, in general, polymeric materials exhibit less toxicity than smaller molecules, which more readily penetrate into cells and tissue. Similarly, small molecules (e.g., dyes) bound to polymeric carriers represent new chemical species that generally are less susceptible to bio-uptake and/or less likely to cause sensitization than the original small molecule. In addition, immobilization of dyes onto suitable polymer carriers may provide improved safety and toxicity compared with the original dye. Polymer-bound dyes may confer several additional benefits including, but not limited to (a) improved solubility and stability of the colorant in a composition, (b) active pH buffering of the composition, (c) controllable viscous and/or viscoelastic properties of the composition, (d) limited water-soluble polymers resists washout and limits or prevents migration into adjacent tissue such as a wound, for example, (e) polymeric emulsifiers avoid the need for additional components to help and/or maintain the stability of an emulsion, and (f) controllable adhesive properties of the composition.

In some embodiments, compositions of the present disclosure comprise a medicament, a liquid vehicle, and a polymeric colorant. In some embodiments, compositions of the present disclosure consist essentially of a medicament, a liquid vehicle, and a polymeric colorant. In some embodiments, compositions of the present disclosure consist of a medicament, a liquid vehicle, and a polymeric colorant. In certain preferred embodiments, the polymeric colorant composition is substantive and resists removal by any constituent of blood or other bodily fluid (e.g., urine, semen, saliva, mucous, tears, sweat, cerebrospinal fluid) as well as saline and other fluids used in surgical irrigation.

Polymeric colorants of the present disclosure comprise a polymer component with at least one colorant component bound thereto. In any embodiment, the colorant component bound to the polymer comprises a chromophore and/or a fluorophore. In some embodiments, the colorant component bound to the polymer comprises a plurality of chromophores. In some embodiments, the colorant component bound to the polymer comprises a plurality of fluorophores. In some embodiments, the colorant component bound to the polymer consists essentially of a chromophore. In some embodiments, the colorant component consists essentially of a plurality of chromophores. In some embodiments, the colorant component bound to the polymer consists essentially of a fluorophore. In some embodiments, the colorant component consists essentially of a plurality of fluorophores. In some embodiments, the colorant component bound to the polymer consists of a chromophore. In some embodiments, the colorant component consists of a plurality of chromophores. In some embodiments, the colorant component bound to the polymer consists of a fluorophore. In some embodiments, the colorant component consists of a plurality of fluorophores. In some embodiments, the colorant component bound to the polymer consists essentially of a chromophore and a fluorophore. In some embodiments, the colorant component bound to the polymer consists of a chromophore and a fluorophore.

A variety of dyes are suitable for use as a colorant component to produce polymeric colorants of the present disclosure. Suitable dyes include those having a chromophore and/or a fluorophore. Nonlimiting examples of suitable dyes include a phthalocyanine dye, an acid dye, a basic dye, an azo dye, an anthroquinone dye, a naphthalimide dye, a coumarin dye, a xanthene dye, a thioxanthene dye, a naphtholactam dye, an azlactone dye, a methine dye, an oxazine dye, a thiazine dye, a triphenylmethane dye, a reactive dye, a direct dye, a vat dye, a sulfur dye, a disperse dye, a mordant dye, and a fluorescent dye. Suitable dyes include, but are not limited to, Reactive Blue 4, Reactive Yellow 2 dye, Disperse Yellow 7, Disperse Yellow 13, Lissamine rhodamine B, PROCION RED MX-5B, Disperse Yellow, malachite green, Lissamine rhodamine B, REACTINT Green, and REACTINT Orange.

It will be recognized by a person having ordinary skill in the art that polymeric colorants of the present disclosure should not react, either directly or indirectly, under ambient storage and/or use conditions with another component (e.g., a medicament, an excipient, an optional ingredient) in the composition to cause a substantially negative effect on the function of the polymeric colorant or the component (e.g., the medicament, the excipient, the optional ingredient). "React directly" and the like are terms used herein to describe a capability of a compound (e.g., colorant component) to participate directly in a chemical reaction with another component (e.g., the medicament) of the composition, whereby the colorant component and/or the other component of the composition is chemically altered and/or the intended function of the colorant component or the other component is substantially deteriorated by the reaction. Another example of a direct reaction that may cause a substantial negative effect is the formation of a complex (e.g. through ionic binding interactions) that, in some instances may interfere with the function of the colorant component and or the medicament (e.g., by causing precipitation of the complex). "React indirectly" and the like are terms used herein to describe a capability of a compound (e.g., colorant component) to generate a chemical species which reacts with another component (e.g., the medicament) of the composition, whereby reaction with the chemical species causes the colorant component and/or the other component (in particular, the medicament) of the composition to be chemically altered and/or whereby reaction with the chemical species causes substantial deterioration of the intended function of the colorant component or the other component. For example, some photosensitive dyes are capable of generating reactive oxygen species (e.g., singlet oxygen) under ambient conditions of light and air. The production of these highly reactive species would be expected to cause undesirable chemical changes to the medicament and/or excipients upon storage and/or use.

The (direct or indirect) reactivity between a polymeric colorant and another component (e.g., a medicament, an excipient) of the composition can be determined, for example, by ambient or accelerated aging studies (usually, not heating excessively, which may cause reactions to occur that would not likely occur over a 2-year shelf life) and subsequent chemical and/or functional analyses of the components of the composition.

In some embodiments, the polymeric colorant of the present disclosure comprises a chromophore component. The chromophore is capable of selective light absorption resulting in the coloration of the polymer. In some embodiments, the chromophore comprises a dye.

Commercially-available triazine dyes, or salts thereof, that can be used to make polymeric colorants include, for example, blue dyes (e.g., Reactive Blue 4, shown in Structure I, available from Sigma-Aldrich, St. Louis, Mo.), yellow dyes (Reactive Yellow 2, shown in Structure II, available from Novact Corporation, Miami, Fla.), and red dyes (PROCION RED MX-5B, shown in Structure III, available from Sigma-Aldrich). Mixtures of two or more polymeric colorants produced from these dyes, other similarly-colored dyes, or other-colored dyes (e.g., green dyes, orange dyes, violet dyes) can be used to produce compositions with a broad range of spectral absorbance properties. Advantageously, this permits the user to select one or more polymeric colorants in a composition, whereby the color of the polymeric colorant or color of a mixture of different polymeric colorants provides optimal detection of the composition on skin having practically any color; including detection of the composition on skin that is colored, intensely colored (e.g., high in melanin content) and/or discolored (e.g., highly discolored) by the presence of a bruise, a birth mark, or a tattoo, for example.

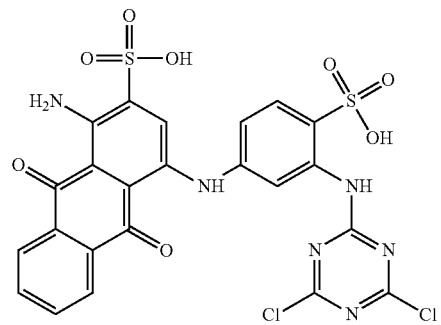

Structure I

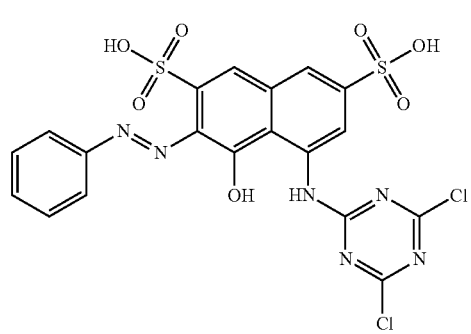

Structure II

Structure III

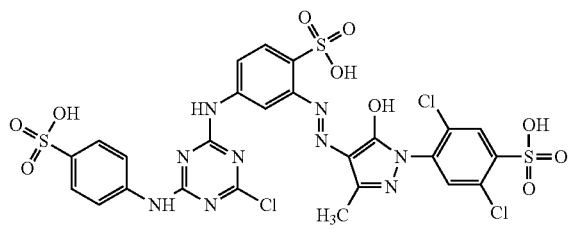

Polymeric colorants of the present disclosure may comprise fluorophores bound to the polymer component. Examples of suitable dyes with fluorophores include, but are not limited to acridine dyes, cyanine dyes, fluorone dyes, oxazin dyes, phenanthridine dyes, rhodamine dyes and the like. Fluorescent polymeric colorants can be observed on a surface (e.g., a skin surface) by illuminating the surface with a light source that emits a wavelength (e.g., an ultraviolet wavelength) suitable to cause the fluorophore to fluoresce.

Although a variety of reactive chemistries exist for coupling dyes onto polymeric surfaces, the covalent coupling of chlorotriazinyl dyes with polymers having reactive amine or hydroxyl functional groups is a non-limiting example of a method to produce polymeric colorants of the present disclosure. Chloro-triazine dyes readily react with primary or secondary amines (e.g., the amine groups found in a linear or a branched polyethyleneimine (PEI) polymer) through the reaction shown in Scheme I, for example:

Scheme I

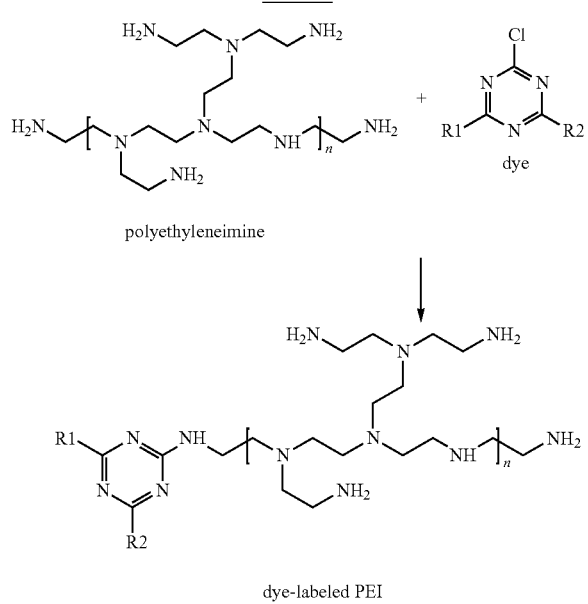

Polymeric colorants of the present disclosure comprise a polymer component and a colorant component. In any embodiment, the polymer component may be derived from a variety of monomers including, for example, vinyl monomers, and, in particular, acrylate monomers. In any embodiment, the polymer component may comprise a synthetic polymer. In any embodiment, the polymer component may comprise a polyamide polymer, a polyamine polymer, a polyethyleneimine polymer, a polyurethane polymer, a polyether polymer, or a polyacrylate polymer as well as copolymers such as a polymer derived from acrylate monomer(s) and other vinyl monomers such as N-vinyl pyrrolidone, N-vinyl caprolactam, ethylene, propylene, styrene, vinyl acetate, and the like. Macromers also may be used such as PEG macromers (M-90G and AM90G from Shin-Nakamura (Wakayama, Japan)) and silicone (e.g. PDMS) macromers. In any embodiment, the polymer component may comprise a natural polymer (e.g., a polysaccharide or polypeptide polymer). Polypeptide polymers may include, for example, proteins derived from plants, such as zein and soy protein. In any embodiment, the polymeric component can comprise a condensation polymer (e.g., a polyamide, a polyester).

Polymer components that include pendant and/or terminal amine or hydroxyl groups suitable for the above chemistry include, for example, linear or branched polyethyleneimine (PEI), polyvinyl alcohol (PVA), dextrans and other carbohydrates, polyethylene glycols (PEG), polypropylene glycol (PPG), and synthetic polypeptide species.

In certain preferred embodiments, polymer components that impart additional utility (i.e., utility other than their function as a polymeric anchor for a colorant component) within a composition. For example, preparations of polyhexamethylene biguanide (PHMB) oligomers, which have antimicrobial properties, contain a mixture of molecules, about half of which include suitable end groups to participate in a reaction with a colorant dye, as shown above. In addition, polymers such as PEI or amphoteric polypeptides (e.g., proteins) can serve as pH buffering reagents to better stabilize pH changes, for example during aging. PEG polymers can stabilize compositions of chlorhexidine gluconate (CHG) and disperse the antimicrobial within otherwise incompatibly hydrophobic environments. In the case of PEI the additional positive charges present on the polymer can also help stabilize (e.g., shield) anionic dyes, thereby making the dyes less likely to cause the precipitation of CHG out of a solution containing both the polymeric colorant and the CHG.

Polymeric colorants of the present disclosure may be prepared in a variety of ways that are known in the art. For example, the polymers may be prepared by including one or more dye-containing (e.g., chromophore-containing and/or fluorophore-containing) monomers in a polymerization reaction, for example, an addition or condensation polymerization, so as to incorporate the chromophore component and/or fluorophore component into the polymer. For example, chromophore-containing vinyl monomers may be included in free radical polymerization reactions to produce homo- or co-polymers incorporating the dye-containing monomers. As another example, hydroxy functional dye-containing monomers may be reacted with isocyanate functional prepolymers or polymers to produce polyurethanes incorporating the dye-containing monomers. Typically, the chromophore will comprise less than 50% of the molecular weight of the polymeric colorant and often less than 40%, 30%, 20% or even 10% of the polymeric colorant by weight.

Polymeric colorants may alternatively be made by reacting an appropriately-substituted dye-containing compound (e.g., chromophore molecule and/or fluorophore-molecule) or precursor thereof with a polymer (as occurs in grafting of a dye molecule onto a polymer).

Polymeric colorants may alternatively be made by reacting a suitable chromophore having reactive functionality with a polymerizable monomer. In these reactions, the chromophore may serve as an "initiator" of the polymer (not to be confused with a free radical initiator). For example, a chromophore having one or more alcohol or amine groups may be reacted with ethylene oxide and/or propylene oxide to form a chromophore bound polyether polymeric colorant.

In general, the composition includes a sufficient amount of polymer-bound colorant to provide an optical indication of a surface area (e.g., skin or mucous membrane) to which it is applied. The optical indication may be observed visually or via an imaging device (e.g., a camera). In some embodiments, the optical indication may be observed by illuminating the area with a light source (e.g., an ultraviolet light source) and observing fluorescence emitted by the polymer-bound colorant.

A person having ordinary skill in the art will recognize the average number of colorant groups per polymer molecule generally can be controlled by the conditions (e.g., starting materials, concentrations, reaction temperature, reaction time) used to synthesize the polymeric colorant. In some embodiments, the average number of groups of a particular colorant can be less than one group bound per polymer molecule. In some embodiments, the average number of groups of a particular colorant can be about one group bound per polymer molecule. In some embodiments, the average number of groups of a particular colorant can be up to about two groups bound per polymer molecule. In some embodiments, the average number of colorant groups can be up to about three groups bound per polymer molecule. In some embodiments, the average number of colorant groups can be up to about five groups bound per polymer molecule. In some embodiments, the average number of colorant groups can be more than five groups bound per polymer molecule. In any embodiment, each polymer molecule may have one or more of a particular chromophore group and/or one or more of a particular fluorophore group bound thereto. Additionally or alternatively, each polymer molecule of the polymeric colorant may have one or more each of first and second chromophore groups and/or one or more each of first and second fluorophore groups bound thereto.

In some embodiments, compositions of the present disclosure may comprise first and second polymeric colorants. Each of the first and second polymeric colorants may be prepared as disclosed herein and may differ from each other in a variety of ways including, for example, the composition and/or size of the polymer component, the composition of colorant component, the linkage of the colorant component to the polymer component, the ratio of colorant component(s) to polymer component, and any combination of any two or more of the foregoing conditions.

In some embodiments, the polymeric component may be capable of forming an adherent, continuous, and preferably pliable film on dry skin. Alternatively, one or more film forming polymers may be added to the composition along with the polymeric colorant. The polymeric colorant and/or added film forming polymer may be soluble or dispersible in the composition. Preferred dispersions are physically stable and do not require shaking prior to use. In some embodiments the film-forming polymeric colorant is capable of forming a self-supporting film with a dry thickness of 50 microns. Suitable film-forming polymers include, for example, polymers derived from vinylic polymers and in particular acrylate monomers such as those described in U.S. Pat. Nos. 6,838,078; 4,584,192; 4,542,012; 7,459,167; and 6,605,666; each of which is incorporated herein by reference in its entirety. In some embodiments, additionally or alternatively, a composition of the present disclosure can further comprise non-colored (and/or nonfluorescent) film-forming polymers. Advantageously, these non-colored (and/or non-fluorescent) polymers can promote the formation of a self-supporting film in which (or onto which) the polymeric colorant can be incorporated, thereby providing a substantive composition to promote the stability and/or durability of the polymeric colorant.

In some embodiments, the polymeric colorant is water-soluble or water-dispersible. Advantageously, water-soluble or water-dispersible colorants can exist in a relatively stable, uniform distribution in an aqueous liquid vehicle. In some embodiments, a polar chromophore and/or fluorophore component can be covalently coupled to a polymer component that is otherwise insoluble or non-dispersible in water, thereby rendering the polymeric colorant water-soluble or water-dispersible.

In some embodiments, the polymeric colorant is water-insoluble. In these embodiments, the polymeric colorant may be used as a dispersion in an aqueous system or it may be used as a solution or a dispersion in a hydroalcoholic solution. In some embodiments, water insoluble polymers advantageously are capable of making highly substantive films. Polymeric colorants with relatively low aqueous solubility not only can improve substantivity on skin when exposed to bodily fluids, they can additionally or alternatively provide improved compositional stability by limiting interaction between the polymeric colorant and a water-soluble medicament. Notably, the polymeric colorants also may serve at polymeric emulsifiers which help emulsion stability. The polymeric colorant emulsifier may be used to help stabilize water in oil (w/o), oil in water (o/w) or multiple emulsions. Stabilization of water in oil emulsions is illustrated in the Examples section.

Compositions of the present disclosure include a medicament. A large variety of medicaments are suitable for use in compositions of the present disclosure. The medicaments include, for example, an antimicrobial agent, an antiseptic, an antibiotic, an analgesic, a steroid, a growth factor, or chemotactic agents. A list of other possible medicaments that may be used in the composition (e.g., in an aerosol-delivered composition) include a thrombolytic agent, a fibrinolytic agent; an antimicrobial agent or antibiotic; analgesics such as aspirin, methyl salicylate, camphor, menthol, a lower alcohol such as ethanol or isopropanol; local anesthetics such as lidocaine, benzocaine, priolocane, mixtures of these such as EMLA and the like; dexamethasone, dexamethasone sodium phosphate, dexamethasone acetate or another dexamethasone derivative, or another anti-inflammatory steroid or non-steroidal anti-inflammatory agent; a peptide, a protein, an enzyme (e.g., a proteolytic enzyme, collagenase, papain), a therapeutic quantity of a chaotropic agent (e.g., urea), and an antiviral agent.

Medicaments of the present disclosure include therapeutically-effective concentrations of one or more active agent that causes a local or systemic therapeutic biological response. The concentration of the medicament in the composition may be therapeutically effective before evaporation of the liquid vehicle, during evaporation of the liquid vehicle and/or after evaporation of the liquid vehicle. Medicaments of the present disclosure do not include bleaching agents, artificial tanning agents, tanning accelerants, or sunscreen agents.

The medicament should be compatible with the other components of the composition. A skilled person will recognize that the other components should not substantially interfere with the action of the medicament (e.g., by inactivation of the medicament; by sequestration of the medicament in a way that makes it substantially less accessible to the cells, tissue, organs or organisms).

A preferred medicament is an antimicrobial. The antimicrobial components can be antiseptics, antibiotics, or combinations thereof. In some embodiments, one or more antiseptics are used. Although certain compositions of the present disclosure can have antimicrobial activity without any additional antimicrobial agents because of the incorporation of film-forming polymers that are inherently antimicrobial, additional antimicrobials can be added to the composition if desired. Preferably, the antimicrobial is present in the composition at a therapeutic concentration, in contrast to antimicrobials that are present in a composition as a preservative, as discussed below.

Herein, antiseptics are distinct from preservatives. Preservatives generally are used at very low levels since the purpose of these preservatives is to prevent bacterial growth in the composition, not to kill microbes on or in the tissue. They are typically added at levels less than 1% by weight and most often are at levels much less than 0.1% by weight. Typical preservatives include parabens, formaldehyde donors, 2-phenoxyethanol, benzyl alcohol; acids, such as benzoic acid, sorbic acid, citric acid, and salts thereof; quaternary ammonium surfactants such as benzalkonium chloride, and the like. When used on colonized or infected tissue at the industry standard preservative concentrations they would not achieve adequate antimicrobial activity.

A variety of antimicrobial agents may be included as long as they are compatible with the compositions (e.g., the components of the composition do not substantially prevent the activity of the antimicrobial agent, the antimicrobial agent does not substantially prevent the optical detection of the polymeric colorant). These antimicrobial agents include, but are not limited to, biguanides such as chlorhexidine salts such as chlorhexidine gluconate (CHG) and alexidine salts such as alexidine hydrochloride, and other cationic antiseptics disclosed in U.S. patent application Ser. No. 10/936,135, which is incorporated herein by reference in its entirety; phenolic antiseptics such as parachlorometaxylenol (PCMX), triclosan, hexachlorophene, and others disclosed in U.S. patent application Ser. No. 10/936,171, which is incorporated herein by reference in its entirety; fatty acid monoesters of glycerin and propylene glycol such as glycerol monolaurate, glycerol monocaprylate, glycerol monocaprate, propylene glycol monolaurate, propylene glycol monocaprylate, propylene glycol monocaprate, as well as other antimicrobial lipids disclosed in U.S. patent application Ser. No. 10/659,571, which is incorporated herein by reference in its entirety; hydrogen peroxide, natural oil antiseptics disclosed in U.S. patent application Ser. No. 10/936,133, which is incorporated herein by reference in its entirety; surfactants and polymers that include a (C12-C22) hydrophobe and a quaternary ammonium group, polyquaternary amines such as polyhexamethylene biguanide, quaternary silanes, silver, silver salts such as silver chloride, silver oxide and silver sulfadiazine, octenidene, benzalkonium halides, cetyl pyridium halides, and the like, as well as combinations thereof. Various combinations of antimicrobial agents can be used in the compositions of the present disclosure. Suitable antiseptics include, for example: antimicrobial lipids; phenolic antiseptics; cationic antiseptics; iodine and/or iodophors; peroxide antiseptics; antimicrobial natural oils; or combinations thereof. These antiseptics are preferably present at a concentration greater than 0.1 wt/wt % and preferably at least 0.25 wt/wt % of the composition. Many compositions of this disclosure have the antiseptic present at greater than 0.5 wt/wt % or even 1.0 wt/wt % of the composition.

Examples of preferred antibiotics include neomycin sulfate, bacitracin, mupirocin, polymyxin, gentamycin, nitrofurantoin, sulfamethoxazole trymethoprim, rifampin, tetracycline, lysostaphin, and combinations thereof. Suitable antibiotic agents include, but are not limited to, beta-lactam antibacterials such as natural and synthetic penicillin type agents including penam penicillins (such as benzyl penicillin, phenoxymethyl penicillin, coxacillin, nafcillin, methicillin, oxacillin, amoxycillin, temocillin, ticarcillin, and the like), penicillinase-stable penicillins, acylamino and carboxypenicillins (such as piperacillin, azlocillin, mezlocillin, carbenicillin, temocillin, ticarcillin, and the like), and broader spectrum penicillins (such as streptomycin, neomycin, framycetin, gentamicin, apramycin, amikacin, spectinomycin, amoxycillin, ampicillin, and the like), cephalosporins, macrolides (such as tylosin, tilmicosin, aivlosin, erythromycin, azithromycin, spiramycin, josamycin, kitasamycin, and the like), lincosamides (such as lincomycin, clindamycin, pirlimycin, and the like), pleuromutilins (such as tiamulin, valnemulin, and the like), polypeptides, glycopeptides (such as vancomycin, and the like), polymyxins (such as polymyxin B, polymyxin E and the like), sulfonamides (such as sulfamethazine, sulfadiazine, silver sulfadiazine, sulfatroxazole, sulfamethoxypyridazine, sulfanilamide, sulfamethoxazole, sulfisoxazole, sulfamethizole, mafenide, and the like, alone or in combination with trimethoprim), chloramphenicol, thiamphenicol, florfenicol, tetracycline type agents (such as tetracycline, chlortetracycline, oxytetracycline, domeclocycline, doxycycline, minocycline, and the like), quinolones and fluoroquinolones (such as ciprofloxacin, enoxacin, grepafloxacin, levofloxacin, lomefloxacin, norfloxacin, ofloxacin, sparfloxacin, trovafloxacin, cinocacin, nalidixic acid, and the like), tiamulin, colistin, meropenem, sulbactam, tazobactam, methacycline, pyrimethamine, sulfacetamide, oxazolidinones, e.g., eperezolid, linezolid, N-((5S)-3-(3-fluoro-4-(4-(2-fluoroethyl)-3-oxy-1-p-iperazinyl)phenyl-2-oxy-5-oxazolidinyl)methyl)acetamide, (S)—N-((3-(5-(3-pyridyl)thiophen-2-yl)-2-oxy-5-oxazolidinyl)methyl)acetamide, 2,2-difluoro-N-({(5S)-3-[3-fluoro-4-(4-glycoloylpiperazin-1-yl)pheny-1]-2-oxo-1,3-oxazolidin-5-yl}methyl)ethanethioamide, (S)—N-((3-(5-(4-pyridyl)pyrid-2-yl)-2-oxy-5-oxazolidinyl) methyl)acetamide hydrochloride, and the like, aminoglycosides (kanamycin, tobramycin, netilmicin, and the like), aminocyclitols, amphenicol, ansamycin, carbaphenern, cephamycin, rifampicin, monobactam, oxacephem, streptogramins (such as quinupristin, dalfopristin, and the like), cycloserines, mupirocin, urea hydroxamates, folic acid analogs (such as trimethoprim, and the like), antibiotic-type antineoplastic agents (such as aclarubicin, actinomycin D, actinoplanone, aeroplysinin derivative, Nippon Soda anisomycins, anthracycline, azino-micyin-A, busucaberin, bleomycin sulfate, bryostatin-1, calichemycin, chromoximycin, dactinomycin, daunorubicin, ditrisarubicin B, doxorubicin, doxorubicin-fibrinogen, elsamicin-A, epirubicin, erbstatin, esorubicin, esperamicin-A1b, fostriecin, glidobactin, gregatin-A, grincamycin, herbimycin, idarubicin, illudins, kazusamycin, kesarirhodins, menogaril, mitomycin, mitoxantorone, mutamycin, mycophenolate mofetil, neoenactin, oxalysine, oxaunomycin, peplomycin, pilatin, pirarubicin, porothramycin, pyrindamycin A, rapamycin, rhizoxin, rodorubicin, sibanomicin, siwenmycin, sorangicin-A, sparsomycin, steffimycin B, talisomycin, terpentecin, thrazine, tricrozarin A, zorubicin, systemic antibacterials (such as 2,4-diaminopyrimidine), nitrofuran sulfones, narbofloxacin, and the like, and combinations thereof. If an antibiotic is used in compositions of the present disclosure, it may be used in combination with an antiseptic. The purpose of the antibiotic like the antiseptics is to kill microorganisms on or in mammalian tissue. They are not present as a preservative. Thus, compositions comprising antibiotics will have them present at greater than 0.1, 0.25, 0.5 and even 1.0% by weight. The concentration will depend on the composition, the antibiotic and the microorganism to be killed. Antiseptics are preferred over antibiotics since they are much less prone to resistance formation, faster acting, and often have a broader spectrum of antimicrobial activity than antibiotics.

For compositions wherein the medicament includes an antimicrobial agent, a particularly important property of the compositions is the ability to reduce the bacterial load on tissue, particularly skin, i.e., to kill the natural skin flora, rapidly. Preferably, antiseptic compositions of the present disclosure are capable of reducing normal skin flora by at least about 1 $\log_{10}$ (i.e., 10-fold), more preferably by at least about 1.5 $\log_{10}$, and most preferably by at least about 2 $\log_{10}$ (i.e., 100-fold), in 2 minutes on a dry human skin site (typically, skin on an abdomen or back) using ASTM testing method E1173-93 and a 30-second scrub with gauze soaked in the composition using moderate pressure.

Compositions of the present disclosure optionally may comprise other optional ingredients that may be delivered to the skin using a composition of the present disclosure and include components of cosmetic compositions. These include, but are not limited to, emollients, humectants, conditioners, moisturizers, vitamins, herbal extracts, antioxidants, exfoliants such as α-hydroxy acids or β-hydroxy acids, emulsifiers, skin soothing agents, and skin sensates, and combinations of any two or more of the foregoing ingredients.

Preferred compositions of the present disclosure are also generally substantive. More preferred compositions of the present disclosure are substantive while in moist environments, such as the vaginal vault and remain in the vagina for longer periods of time than typical antiseptics such as BETADINE 10% povidone-iodine solution (Purdue Frederick, Norwalk, Conn.). A "substantive" composition is one that when tested as described above resists removal for at least about 15 seconds. Preferably, the compositions are even more substantive and resist being removed under the same conditions for at least about 30 seconds, more preferably at least 45 seconds, and most preferably at least about 60 seconds. This is conveniently determined by observing, at the site to which it was applied, the sustained presence of color associated with the polymeric colorant in the composition.

In some embodiments, compositions of the present disclosure comprise film-forming polymers. Optionally, the film-forming polymer may comprise the polymeric colorant. One or more film-forming polymers may be included in the compositions of the present disclosure to improve substantivity (e.g., resistance to wash off by blood and body fluid exposure), improve adhesion of PSA-coated products, and/or reduce the tack of the compositions. Preferred film-forming polymers of the compositions of the present disclosure are substantive and resist removal by prolonged exposure to fluids such as water, saline, and body fluids, yet can be easily and gently removed without the need for organic solvents. Suitable preferred film-forming polymers for use as polymeric colorants according to the present disclosure are described in U.S. Pat. No. 6,838,078, which is incorporated herein by reference in its entirety.

Compositions of the present disclosure may incorporate film-forming polymers that have both hydrophilic and hydrophobic moieties. Preferably, the film-forming polymers are prepared from at least two monomers (i.e., a hydrophilic monomer and a hydrophobic monomer), and more preferably from at least three monomers. The term "hydrophobic monomer" as used herein refers to a monomer which, if homopolymerized, would not be soluble in water at room temperature to more than about 0.25 wt-%. Preferably, such polymers have a molecular weight of about 8,000 Daltons to about 250,000 Daltons when examining for solubility.

The dried films of compositions of the present disclosure are generally flexible and durable. That is, they do not crack or flake off the skin as brittle films might do. Significantly, the film-forming vinyl polymer contributes to achieving a delicate balance between low tack and flexibility.

Generally, compositions are applied to the tissue, typically skin, and allowed to dry and remain in place for at least 2 minutes, and often for several hours to days. Significantly, many of the antiseptic compositions of the present disclosure maintain very low bacterial counts on the tissue, typically skin, for long periods of time, e.g., often up to 6 hours, and even up to 24 hours.

Compositions of the present disclosure comprise a liquid vehicle. Suitable liquid vehicles include water, optionally in combination with acetone or an alcohol, particularly a (C1-C4) alcohol (i.e., a lower alcohol) such as ethanol, 2-propanol, and n-propanol, and mixtures thereof. The preferred liquid vehicle is injectable-grade water, i.e., USP grade "water for injection"; however, other forms of purified water may be suitable such as distilled and deionized water.

For applications to intact skin, however, it may be desirable to include a lower alcohol such as ethanol, isopropanol, or n-propanol. These alcohols are well known to have antiseptic activity and to contribute to rapid microbial kill. For these applications the alcohol to water ratio is preferably at least about 60:40, and more preferably at least about 70:30, by weight. Addition of alcohol in these high concentrations can also decrease the dry time of the composition on the skin, when desired.

When a lower alcohol is used, incorporation of surfactants may or may not be necessary. In some embodiments, the addition of a surfactant can improve antimicrobial efficacy, as described in U.S. Pat. No. 7,147,873, which is incorporated herein by reference in its entirety. Notably, anionic and zwitterionic surfactants can be particularly effective at enhancing the antimicrobial efficacy. Inclusion of ionic or nonionic surfactants can be used to increase compatibility of medicament or polymeric colorant with the vehicle solution. Examples of nonionic surfactants useful in this role may include polyethoxylates, nonyl phenyl polyethoxylates, alkyl esters, alkyl polyethoxylates, and PEG-PPG copolymers. Examples of ionic surfactants include alkyl or aryl quaternary ammonium compounds, alkyl or aryl amines, fatty acid salts, aryl or alkyl sulfonates.

Certain preferred compositions, particularly for use on mucosal tissue, include water and are substantially free (i.e., less than about 10 wt-%; more preferably, less than about 5%; even more preferably, less than about 3%) of volatile organic solvents (i.e., those having a closed-cap flash point of greater than about 140° F. (60° C.)), such as acetone, lower alcohols, alkanes, volatile silicones, etc. The addition of lower alcohols (C1-C4) at less than about 4 wt-% may improve wetting of the compositions and yet maintain a flashpoint above about 140° F. (60° C.). Flashpoint is measured according to test method ASTM D3278-96.

Aqueous formulations are preferred since these formulations are gentle to both skin and mucosal tissue and may even be suitable for use on open wounds as a wound cleanser.

Compositions of the present disclosure can be placed into containers, preferably sealed containers, such as frangible pouches or ampoules.

Kits are also contemplated. In any embodiment, a kit may include instructions for preparing a skin site for a surgical procedure. In any embodiment, a kit may include instructions for treating a medical condition. Kits of the present disclosure may comprise a sealed container containing any composition of the present disclosure. In these embodiments, the composition comprises a medicament, a vehicle, and at least one polymeric colorant that includes a polymer component with a colorant component bound thereto, as described herein. The colorant component is not a photosensitizer dye capable of producing singlet oxygen. The medicament can be selected according to the method (e.g., preparation of a skin site for surgery or for the treatment of a medical condition) in which the contents of the kit will be used. In some embodiments, the kit may further comprise an applicator to apply the composition to a treatment area. The applicator may be adapted to be operationally coupled to the sealed container containing the composition.

In any embodiment of the kit, the medicament may comprise an antimicrobial agent wherein, when the composition is contacted for a period of time with an area of a surface (e.g., a skin surface), having a number of cultivable microorganisms present thereon, the concentration of antimicrobial agent in the liquid vehicle is sufficient to reduce the number of cultivable microorganisms in the area. In any embodiment, the kit further can comprise a plurality of sealed containers, each of the plurality of containers containing the composition. In some embodiments, the plurality of sealed containers may comprise a first container containing a first composition having a first polymeric colorant and a second container containing a second composition having a second polymeric colorant. The first and second compositions may comprise the same medicament or a different medicament.

In any embodiment, the kit may further comprise a rinse or remover composition for removing the composition from a treated surface (e.g., a treated skin surface). In some embodiments, the rinse solution can contain water (e.g., deionized water or water for injection). The rinse solution may further comprise a component (e.g., soap; an organic solvent acceptable for use on skin, such as ethanol, isopropanol, and/or acetone, for example) to assist the cleaning and removal of the composition. In any embodiment, the rinse solution may further comprise an agent that counteracts an effect of the medicament. That is, in addition to reducing the effect of the medicament by dilution, the rinse may comprise an agent (e.g., a chemical agent) that directly or indirectly inhibits the effect of the medicament.

Compositions of the present disclosure can be used in a variety of methods. In some embodiments, the compositions can be used in a method of preparing a skin site for a medical procedure (e.g., an incision, a percutaneous injection, a percutaneous insertion of a medical device, a surgical procedure). In these embodiments, the composition may comprise a medicament comprising, for example, an antimicrobial agent, an analgesic agent, an anesthetic agent (e.g., a local anesthetic) or a combination of any two or more of the foregoing medicaments. Advantageously, the presence of the colorant in compositions of the present disclosure can provide instantaneous (and, optionally, durable) visible confirmation that the medicament has been applied to the proper area of interest.

In one aspect, the present disclosure provides a method of preparing skin as a site for a surgical procedure (e.g., a surgical incision; a wound closure procedure; a percutaneous insertion of a medical device such as a needle, a cannula, a catheter, a drain tube, a probe, a sensor, an endoscope, an imaging device, or the like). The method comprises providing any of the compositions disclosed herein, wherein the composition includes at least one polymeric colorant comprising a polymer component with a colorant component bound thereto, an antimicrobial agent, and a liquid vehicle. The method further comprises applying the composition to an area of skin selected for the surgical procedure and verifying the area to which the composition was applied by observing on the skin a color associated with the composition. In some embodiments, observing a color associated with the composition comprises observing the color by using an unaided human eye. In some embodiments, observing a color associated with the composition can comprise obtaining an image of the area to which the composition was applied and observing the image by using a human eye. The antimicrobial agent is present at a sufficient concentration in the composition such that, when the composition (e.g., a predetermined quantity of the composition) is contacted with an area of skin (e.g., a predetermined area of skin) having a number of cultivable microorganisms present thereon, the antimicrobial agent is capable of reducing the number of cultivable microorganisms. Optionally, the composition may further comprise an anesthetic or analgesic agent to further provide pain reduction or relief. A person having ordinary skill in the art will recognize that reducing the number of cultivable microorganisms on the skin is a function of the amount of antimicrobial agent to which the microorganisms are exposed and the amount of time to which the microorganisms are exposed to the antimicrobial agent. Preferably, applying compositions of the present disclosure results in reducing normal skin flora by at least about 1 $\log_{10}$ (i.e., 10-fold), more preferably by at least about 1.5 $\log_{10}$, and most preferably by at least about 2 $\log_{10}$ (i.e., 100-fold), in 2 minutes on a dry human skin site (typically, skin on an abdomen or back) using ASTM testing method E1173-93 and a 30-second scrub with gauze soaked in the composition using moderate pressure.

In another aspect, the present disclosure provides a method of treating a medical condition. The method comprises providing any of the compositions disclosed herein, wherein the composition includes at least one polymeric colorant comprising a polymer component with a colorant component bound thereto, a medicament, and a liquid vehicle. The method further comprises applying the composition to a treatment area (e.g., an area of skin) and verifying the area to which the composition was applied by observing on the area (e.g., skin) a color associated with the composition. In some embodiments, observing a color associated with the composition comprises observing the color by using an unaided human eye. In some embodiments, observing a color associated with the composition can comprise obtaining an image of the area to which the composition was applied and observing the image by using a human eye. The medicament comprises an active agent in a quantity sufficient to elicit a preselected biological response other than reducing the number of cultivable microorganisms on skin. Nonlimiting examples of suitable medical treatments that can be performed using the present method include the chemical and/or enzymatic debridement of tissue (e.g., burned or necrotic skin); localized pain reduction; localized inflammation reduction; localized thrombolysis; delivery of a drug to a localized area; treatment vaginal infections such as yeast or bacterial vaginosis, and the like; and the delivery of a systemic drug. In some embodiments, the medical condition may be a skin condition (e.g., a localized skin condition such as psoriasis, roseacea, impetigo or other skin infections). In any of the embodiments of the method, the preselected biological response may be substantially localized at the skin site (e.g., by using a poorly-absorbed and/or substantially nondiffusible medicament).

Preferably, an effective amount of the composition, when applied to a predetermined region of a body, is transparent or translucent such that, during application of the composition, the skin and any visible markings (e.g., pre-surgical markings to denote a surgical site and/or an anatomical landmark) and/or anatomical features (e.g., a mole, a lesion, a contusion, or the like) can be visually observed through the applied layer of the composition. In addition, it is preferred that, after application of an effective amount of the composition and after absorption or evaporation of any portion of the liquid vehicle, the skin and any visible markings and/or anatomical features can be visually observed through the applied layer of the composition.

In any embodiment, the methods further may comprise performing a percutaneous insertion of a medical device. In any embodiment of the methods, applying the composition to the skin site may comprise applying the composition in the form of a liquid, aerosol or foam. Suitable foaming agents include, for example, silicone copolyols and fluorinated surfactants. Applicators for applying liquid compositions to skin are known in the art and these applicators may be used to apply compositions of the present disclosure. Nonlimiting examples of suitable applicators include the applicators described in U.S. Pat. Nos. 5,435,660; 6,248,085; 7,261,701; 7,377,710; 6,672,704; and 6,422,778; each of which is incorporated herein by reference in its entirety.

In any embodiment of the methods, the method further can comprise removing the composition from the area to which it is applied. This process can be done using a rinse solution (e.g., water, optionally containing soap and/or a suitable organic solvent such as alcohol, isopropanol, or acetone, for example). Advantageously, the removal of the composition can be verified by observing the presence or absence of polymeric colorant in the area being rinsed. Thus, in some embodiments, the method further comprises, after the rinse step, the step of verifying the removal of the composition by observing the presence or absence of a color associated with the polymeric colorant in the area to which the composition was applied. Advantageously, polymeric colorants of the present disclosure may significantly reduce staining of the skin. Many of the preferred compositions can be removed with soap and water or ethanol/water solutions with little or no visible remaining residue.

A further advantage of the polymeric colorants of this disclosure is their use in presurgical and pre-intravenous skin antiseptic preps. In these and similar applications around an open wound it is particularly advantageous to prevent dye from entering the wound. The polymeric colorants of this disclosure, particularly those that are oil soluble and water insoluble (soluble at less than 1% in water) will resist removal and migration due to exposure to blood and body fluids. "Oil soluble" as used herein means the polymeric colorant dissolves in a cosmetic emollient oil such as isopropylmyristate NF to generate a clear transparent solution at a concentration of 5% solids. Preferred polymers are soluble in IPM at even higher concentrations such as 10% wt/wt or more.

Embodiments

Embodiment 1 is a composition, comprising:
at least one polymeric colorant comprising a polymer component with at least one colorant component covalently bound thereto;
a medicament; and
a liquid vehicle;
wherein the at least one colorant component does not react directly or indirectly with the medicament.

Embodiment 2 is a composition, comprising:
a first polymeric colorant comprising a first polymer component with a first colorant component bound thereto;
a second polymeric colorant comprising a second polymer component with a second colorant component covalently bound thereto;
a medicament; and
a liquid vehicle;
wherein each of the first and second colorant components does not react directly or indirectly with the medicament.

Embodiment 3 is the composition of embodiment 1 or embodiment 2, wherein at least one colorant component comprises one or more chromophore and/or one or more fluorophore.

Embodiment 4 is the composition of any one of the preceding embodiments, wherein at least one polymer component comprises a natural polymer, a synthetic polymer, a derivative of any of the foregoing polymers, or a mixture of any two or more of the foregoing polymers.

Embodiment 5 is the composition of any one of the preceding embodiments, wherein at least one polymer component is derived from vinyl monomers.

Embodiment 6 is the composition of embodiment 5, wherein the vinyl monomers comprise acrylate monomers.

Embodiment 7 is the composition of any one of the preceding embodiments, wherein at least one polymer component comprises a condensation polymer.

Embodiment 8 is the composition of any one of the preceding embodiments, wherein at least one polymer component comprises a polyamine or a polyamide.

Embodiment 9 is the composition of embodiment 4, wherein the natural polymer is selected from the group consisting of a polysaccharide and a polypeptide.

Embodiment 10 is the composition of embodiment 4, wherein the synthetic polymer selected from the group consisting of a polyethyleneimine polymer, a polyurethane polymer, a polyether polymer, and a polyacrylate polymer.

Embodiment 11 is the composition of any one of the preceding embodiments, wherein at least one polymeric colorant comprises a film-forming polymeric colorant.

Embodiment 12 is the composition of embodiment 11, wherein the film-forming polymeric colorant is capable of forming a self-supporting film with a dry thickness of 50 microns.

Embodiment 13 is the composition of any one of the preceding embodiments, further comprising a film-forming polymer.

Embodiment 14 is the composition of any one of the preceding embodiments, wherein at least one polymeric colorant is water-soluble or water-dispersible.

Embodiment 15 is the composition of any one of the preceding embodiments, wherein at least one polymeric colorant is water-insoluble.

Embodiment 16 is the composition of any one of the preceding embodiments, wherein the polymeric colorant serves as an emulsifier in a water-in-oil emulsion or an oil-in-water emulsion.

Embodiment 17 is the composition of any one of the preceding embodiments, wherein at least one colorant component comprises a dye.

Embodiment 18 is the composition of embodiment 17, wherein the dye is selected from the group consisting of a phthalocyanine dye, an acid dye, a basic dye, an azo dye, an anthroquinone dye, a xanthene dye, a triphenylmethane dye, a reactive dye, a direct dye, a vat dye, a sulfur dye, a disperse dye, a mordant dye, and a fluorescent dye.

Embodiment 19 is the composition of embodiment 18, wherein the fluorescent dye is selected from the group consisting of an acridine dye, a cyanine dye, a fluorone dye, an oxazin dye, a phenanthridine dye, a thioxanthone dye, a rhodamine dye, or a derivative of any one of the foregoing dyes.

Embodiment 20 is the composition of any one of the preceding embodiments, wherein the medicament is selected from the group consisting of an antimicrobial agent, an antiseptic, an antibiotic, an analgesic, a thrombolytic agent, a fibrinolytic agent, a local anesthetic, an anti-cancer chemotherapeutic agent, an enzyme, and a mixture of any of two or more of the foregoing medicaments.

Embodiment 21 is the composition of embodiment 20; wherein the medicament comprises an antimicrobial agent; wherein, when the composition is contacted for a period of time with an area of a surface having a number of cultivable microorganisms present thereon, the concentration of antimicrobial compound in the liquid vehicle is sufficient to reduce the number of cultivable microorganisms on the area of the surface.

Embodiment 22 is the composition of embodiment 21, wherein reducing the number of cultivable microorganisms comprises reducing the number of cultivable microorganisms by a factor of 1 $\log_{10}$ or more.

Embodiment 23 is the composition of embodiment 22, wherein the antimicrobial agent comprises a chemical antiseptic compound.

Embodiment 24 is the composition of embodiment 23, wherein the chemical antiseptic compound comprises an antiseptic alcohol or a cationic antiseptic compound.

Embodiment 25 is the composition of embodiment 24, wherein the cationic antiseptic compound comprises a polycationic antiseptic compound.

Embodiment 26 is the composition of embodiment 25, wherein the cationic antiseptic compound comprises chlorhexidine, polyhexamethylene biguanide, octenidine, or salts thereof.

Embodiment 27 is the composition of embodiment 24, wherein the cationic antiseptic compound comprises a polycationic compound.

Embodiment 28 is the composition of embodiment 27, wherein the polycationic compound comprises polyhexamethylene biguanide, octenidine, or a salt of any of the foregoing polycationic compounds.

Embodiment 29 is the composition of any one of the preceding embodiments wherein the liquid vehicle comprises water.

Embodiment 30 is the composition of embodiment 29, wherein the liquid vehicle further comprises acetone or an alcohol.

Embodiment 31 is the composition of any one of the preceding embodiments, further comprising a foaming agent.

Embodiment 32 is the composition of embodiment 31, wherein the foaming agent is selected from the group consisting of a silicone copolyol and a fluorinated surfactant.

Embodiment 33 is the composition of any one of embodiments 1 through 32 wherein, when applied as a layer onto a predetermined area of a skin surface, the layer formed by an effective amount of the composition is transparent or translucent.

Embodiment 34 is the composition of embodiment 33, wherein the layer is transparent or translucent after absorption and/or evaporation of the liquid vehicle in ambient conditions.

Embodiment 35 is a method of preparing skin as a site for a surgical procedure, comprising:

providing a composition that includes at least one polymeric colorant comprising a polymer component with a colorant component covalently bound thereto, an antimicrobial agent, and a liquid vehicle;

wherein the antimicrobial agent is present at a sufficient concentration in the composition such that, when a predetermined quantity of the composition is contacted with a predetermined area of skin having a number of cultivable microorganisms present thereon, the antimicrobial agent is capable of reducing the number of cultivable microorganisms;

applying the composition to an area of skin selected for the surgical procedure; and verifying the area to which the composition was applied by observing on the skin a color associated with the composition.

Embodiment 36 is a method of treating a medical condition, comprising:

providing a composition that includes at least one polymeric colorant comprising a polymer component with a colorant component covalently bound thereto, a medicament, and a liquid vehicle;

wherein the medicament comprises an active agent in a quantity sufficient to elicit a preselected biological response other than reducing the number of cultivable microorganisms on skin;

applying the composition to an area; and verifying the area to which the composition was applied by observing on the area a color associated with the composition.

Embodiment 37 is the method of embodiment 35 or embodiment 36, wherein observing comprises observing by using an unaided human eye.

Embodiment 38 is the method of embodiment 36, wherein the medical condition is a skin condition.

Embodiment 39 is the method of any one of embodiments 36 through 38, wherein the preselected biological response is substantially localized at the area.

Embodiment 40 is the method of any one of embodiments 35 through 39, further comprising:

after applying the composition to the area, allowing a portion of the liquid vehicle to evaporate or be absorbed;

wherein verifying the area to which the composition was applied by observing a color associated with the composition is performed after the portion of the liquid vehicle is allowed to evaporate or be absorbed.

Embodiment 41 is the method of any one of embodiments 35 through 40; wherein applying the composition comprises applying a layer of the composition; wherein, after applying an effective amount of the composition onto the treatment area and, optionally, allowing a portion of the liquid vehicle to evaporate or be absorbed, the layer is transparent or translucent.

Embodiment 42 is the method of any one of embodiments 35 through 41, further comprising:

visually observing a marking or an anatomical feature through the composition after the composition is applied to the area and, optionally, a portion of the liquid vehicle is allowed to evaporate or be absorbed.

Embodiment 43 is the method of any one of embodiments 35 through 42, further comprising performing a surgical procedure.

Embodiment 44 is the method of embodiment 43, wherein the surgical procedure comprises making an incision, performing a percutaneous injection, or performing a percutaneous insertion of a medical device.

Embodiment 45 is the method of any one of embodiments 35 through 44, wherein applying the composition to the skin site comprises applying the composition in the form of an aerosol or foam.

Embodiment 46 is the method of any one of embodiments 35 through 45, further comprising removing the composition from the area to which it is applied.

Embodiment 47 is a method of killing microorganisms on mammalian skin prior to a percutaneous procedure comprising:

providing a composition that includes at least one polymeric colorant comprising a polymer component with a colorant component covalently bound thereto, an antimicrobial, and a liquid vehicle;
  wherein the antimicrobial is present in a concentration of at least 0.25% wt/wt of the composition;
  applying the composition to an area of mammalian skin; and
  wherein the applying the composition to the area reduces the number of cultivable microorganisms on the mammalian skin;
  verifying, by human eye, the area to which the composition was applied by observing on the area a color associated with the composition.

Embodiment 48 is a kit, comprising:

a sealed container containing a composition that includes a medicament, a liquid vehicle, and at least one polymeric colorant comprising a polymer component with a colorant component covalently bound thereto;
  wherein the at least one colorant component does not react directly or indirectly with the medicament.

Embodiment 49 is the kit of embodiment 48, wherein the at least one colorant component comprises one or more chromophore and/or one or more fluorophore.

Embodiment 50 is the kit of any one of embodiments 48 or embodiment 49, further comprising an applicator for applying the composition to skin.

Embodiment 51 is the kit of any one of embodiments 48 through 50, wherein the medicament comprises an antimicrobial agent; wherein, when the composition is contacted for a period of time with an area of a surface having a number of cultivable microorganisms present thereon, the concentration of antimicrobial agent in the liquid vehicle is sufficient to reduce the number of cultivable microorganisms in the area.

Embodiment 52 is the kit of any one of embodiments 48 through 51, further comprising a plurality of sealed containers, each of the plurality of containers containing the composition.

Embodiment 53 is the kit of embodiment 52, wherein the plurality of sealed containers includes a first container containing a first composition having a first polymeric colorant, wherein the plurality of sealed containers includes a second container containing a second composition having a second polymeric colorant.

Embodiment 54 is the kit of any one of embodiments 48 through 53, wherein the applicator is adapted to be operationally coupled to at least one of the sealed containers.

Embodiment 55 is the kit of any one of embodiments 48 through 54, further comprising a rinse solution.

Embodiment 56 is the kit of embodiment 55, wherein the rinse solution comprises an agent that counteracts an activity of the medicament.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials. Materials utilized in the preparation of the examples are shown in Table 1.

TABLE 1

Materials Table

| Component | Description | Source |
|---|---|---|
| Benzyl alcohol | | Sigma Aldrich; (Milwaukee, WI) |
| CHG | Chlorhexidine gluconate, 20% solution | Xttrium Laboratories; (Mt. Prospect, IL) |
| Disperse Yellow 7 | Dye | Sigma Aldrich |
| Disperse Yellow 13 | Dye | Sigma Aldrich |
| Gluconic acid | | Sigma Aldrich |
| IOA | Isooctylacrylate | 3M Company; (St. Paul, MN) |
| IPM | Isopropyl myristate (Jeenchem IPM NF) | Jeen Chemical, (Fairfield, NJ) |
| IOA/SMA/M-90G (40/40/20) 35% in IPM | Polyacrylate copolymer | Prepared as described in U.S. Pat. No. 7,030,203 |
| Lidocaine hydrochloride | | Sigma Aldrich |
| M-90G | Poly(ethylene glycol) methyl ether methacrylate | Shin-Nakamura Chemicals; (Wakayama, Japan) |
| MRDFD-YGPOAc CAS #650616-86-7 | Yellow dye | prepared as described in U.S. Pat. No. 6,930,184 |
| PHMB | Polyhexamethylene biguanide; Cosmocil CQ | Arch Chemicals; (Norwalk, CT) |
| PEI | Polyethyleneimine | As listed |
| PROCION RED MX-5B | Red dye | Sigma-Aldrich |
| REACTINT green | polyether polymeric colorant | Milliken Chemicals; (Spartanberg, SC) |
| REACTINT orange | polyether polymeric colorant | Milliken Chemicals |
| Reactive Blue 4 | Blue dye | Alfa Aesar (Heysham, Lancashire, UK) |
| Reactive Yellow 2 | Yellow Dye | Sigma Chemical Co.; (St. Louis, MO) |
| SMA | Stearylmethacrylate (Rocryl 330) | Rohm & Haas; (Philadelphia, PA) |
| SOFTCAT SK-MH | | Dow Chemical, (Midland MI) |
| VAZO 67 | Initiator; 2,2' azobis(2-methylbutanenitrile) | Du Pont; (Wilmington, DE) |

Preparative Examples 1-3

Preparation of Polyethyleneimine Polymeric Colorants

Blue, red and yellow colored polyethyleneimine (PEI) dye samples were prepared. A 2% PEI stock solution was prepared by diluting 0.6676 gm of a 30% solution of 70 kD PEI (Polysciences, Inc.; Warrington, Pa.) to 10.0 mL with deionized $H_2O$ (DI $H_2O$). A 2% blue PEI solution (Preparative Example 1) was prepared by mixing 1.6818 gm of a 30% solution of 70 kD PEI (Polysciences) and 0.1299 gm of Reactive Blue 4 dye (40% dye) and diluting to 10.0 mL with DI $H_2O$ to yield a blue solution of polymer-bound dye (the polymer-bound dye comprising 2.0 wt % polymer and 0.21 wt % dye, respectively). This sample was mixed at room temperature for 1 hour. A 2% yellow PEI solution (Preparative Example 2) was prepared by mixing 1.6674 gm of a 30% solution of 70 kD PEI (Polysciences) and 0.0827 gm of Reactive Yellow 2 dye (60% dye) and diluting to 10.0 mL with DI $H_2O$ to yield a yellow solution of polymer-bound dye (the polymer-bound dye comprising 2.0 wt % polymer and 0.20 wt % dye, respectively). This sample was mixed at room temperature for 1 hour. A 2% red PEI solution (Preparative Example 3) was prepared by mixing 1.6709 gm of a 30% solution of 70 kD PEI (Polysciences) and 0.1292 gm of PROCION RED MX-5B dye (50% dye) and diluting to 10.0 mL to yield a red solution of polymer-bound dye (the polymer-bound dye comprising 2.0 wt % polymer and 0.26 wt % dye, respectively). This sample was mixed at room temperature for 1 hour. Reversed-phase HPLC analysis (u.v.—visible detection) of the resulting polymeric colorant solutions showed decreases in the elution peaks for the free dyes concurrent with the development a visible signals corresponding to the dyes during elution of polymeric components, indicating the dyes were quantitatively bound onto the PEI polymer.

Preparative Examples 4-5

Preparation of Thioxanthone Colorant-Bound Polyacrylate Polymer

A stock solution was prepared by mixing IOA (32.0 g), SMA (32.0 g), M-90G (16.0 g), IPA (0.80 g) and VAZO-67 (0.240 g). Twenty grams of the above stock solution was placed into each of two bottles. Yellow dye (MRDFD-YGPOAc, shown in Structure IV) and either toluene or IPM were added to the respective bottles in the amounts shown in Table 2. Both bottles were purged with nitrogen, sealed and were placed in an oven at 85° C. for 40 hours. The viscosity of the polymerized samples was similar to honey. The composition was transparent indicating the solubility in the oil isopropylmyristate.

Structure IV

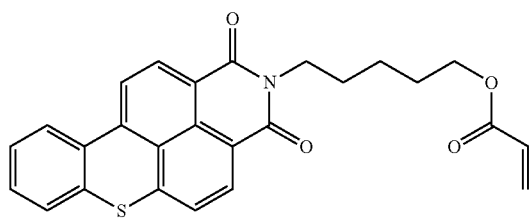

TABLE 2

Components used for Preparative Examples 5 and 6.

| Preparative Example | Stock Soln. (grams) | Solvent (grams) | Yellow Dye | Polymer Solution Appearance |
|---|---|---|---|---|
| PE4 | 20 | IPM (37) | 0.23 g (0.40 wt %) | Clear solution |
| PE5 | 20 | Toluene (37) | 0.57 g (1.0 wt %) | Slightly hazy solution |

Example 1

Composition Comprising Red Polymeric Colorant and Chlorhexidine Gluconate (CHG)

A red colored 2% CHG solution was prepared by diluting 1.0 mL of Xttrium 20% CHG reagent with 0.5 mL of the 2% red PEI solution from Preparative Example 3 and 8.5 mL DI $H_2O$ to yield a 2% CHG solution containing 0.1% PEI polymer. The pH of this solution was pH 8.7. The CHG remained soluble in this higher pH buffered solution.

Example 2

Composition Comprising Two Polymeric Colorants and CHG

A green colored 2% CHG solution was prepared by diluting 1.0 mL of the Xitrium 20% CHG reagent with 0.5 mL of the 2% blue PEI solution (from Preparative Example 1) and 2.0 mL of the yellow PEI solution (from Preparative Example 2). After diluting to 10 mL with DI $H_2O$ the resulting green solution contained 2% CHG and 0.5% PEI, and the pH of the mixture was 9.1. The CHG remained soluble in this higher-pH buffered solution.

Example 3

Buffered Composition Comprising Two Polymeric Colorants and CHG

A green colored 2% w/w CHG green buffered at pH 6.5 solution was prepared by weighing 2.669 gm of Xitrium 20% CHG reagent into a 8 dram vial, where it was treated with 0.981 gm of the 2% blue PEI solution from Preparative Example 1, 4.685 gm of 2% yellow PEI solution from Preparative Example 2 and 15.435 gm of DI $H_2O$. The resulting strongly basic sample was incompletely soluble before addition of 1.64 gm of a 1M solution of 2-(N-morpholino)ethanesulfonic acid (MES, free acid), which immediately solubilized the bulk of precipitate and dropped the pH to 6.5. A small amount of finely divided dark insoluble material was removed by filtration. This precipitated material is believed likely to represent low solubility CHG chloride or sulfate from neutral salts carried in with the crude dye preps used in the original synthesis.

Examples 4-6

Preparation of Polyhexamethylene Biguanide (PHMB) Polymeric Colorants

Blue-colored (Example 4), red-colored (Example 5), and yellow-colored Example 6) polyhexamethylene biguanide samples were prepared. A 54 mg sample of Reactive Blue 4 dye (40% dye) was treated with 2.0 mL (2.01 gm) of 20% PHMB (Cosmocil CQ) and 18.0 mL (18.0 gm) of DI H₂O. One drop of triethylamine (TEA) was also added and the sample was sonicated for 15 min. A 50 mg sample of Reactive Yellow 2 dye (60% dye) was treated with 2.0 mL (2.01 gm) of 20% PHMB (Cosmocil CQ) and 18.0 (18.0 gm) of DI H₂O One drop of triethylamine (TEA) was also added and the sample was sonicated for 15 min. A 51 mg sample of PROCION RED MX-5B (50% dye) was treated with 2.0 mL (2.00 gm) of 20% PHMB (Cosmocil CQ) and 18.0 mL (18.0 gm) of DI H₂O. One drop of triethylamine (TEA) was also added and the sample was sonicated for 15 min. The samples were then heated at 60° C. for 1 hour. After heating all three samples contained significant precipitated material, and the solutions were highly basic. The solutions were acidified with trifluoroacetic acid (until the solution was slightly acidic, as indicated by pH paper) and diluted 1:1 with additional H₂O. The solutions were decanted to remove any precipitated material, yielding clear and strongly-colored approximately 1% PHMB solutions. HPLC analysis of these solutions confirmed the dye was immobilized on a small fraction of the PHMB. The yellow preparation contained some free dye.

Examples 7-8

Emulsion Compositions Comprising a Polymeric Colorant

Emulsions were prepared using the ingredients listed in Table 3. Initially, the water and gluconic acid were mixed and sodium hydroxide (5N) was used to adjust the pH to 6. The CHG solution and SOFTCAT polymer were subsequently added. The resulting mixture was placed on a shaker until the solution was homogenous and the SOFTCAT was dissolved. In a separate vessel all the oil phase components were combined and blended. Any particulates present in the PE4 and PE5 preparations were removed by centrifugation. Both the oil and water phases were placed in an oven and brought to 60 C. The water phase was added to the oil phase slowly (over a 2 min period) while shearing the composition with a rotor/stator Silverson L4R homogenizer set at ⅔ full speed. Each mixture was mixed an additional one minute at full speed using the homogenizer. The homogenized mixtures were rolled overnight. Both emulsions were highly fluorescent and, when spread on a surface as a thin film, could be observed by its fluorescence under ultraviolet light illumination.

TABLE 3

Components used for Examples 7 and 8.

| Component | phase | Example 7 | Example 8 |
|---|---|---|---|
| IPM | oil | 48.71 g | 48.71 g |
| PE-5 | oil | 9.29 g | 0 g |
| PE-6 | oil | 0 g | 9.29 g |
| Benzyl alcohol | oil | 5 g | 5 g |
| Sensiva SC-50 | oil | 1 g | 1 g |
| SOFTCAT SK-MH | water | 0.7 g | 0.7 g |
| Gluconic acid 50% | water | 0.3 g | 0.3 g |
| 20% CHG Solution | water | 20 g | 20 g |
| Water | water | 15 g | 15 g |

Examples 9-10

Emulsion Compositions Comprising a Polymeric Colorant and a Medicament

Using procedures similar to those described in Preparative Examples 4 and 5, red and yellow polymeric colorants can be prepared from Disperse Yellow 13 methacrylate and Disperse Yellow 7 methacrylate, both available from Sigma Aldrich. Furthermore, the resulting polymeric colorants can be used to prepare highly colored antiseptic compositions using the procedures described in Examples 7 and 8.

Examples 11-15

Emulsion Compositions Comprising a Polymeric Colorant and a Medicament

The compositions listed in Table 4 were prepared according to the procedures described in Examples 7-8. The compositions were highly colored. After spreading/painting a thin layer of the prepared dyes on white printer paper the dyes (yellow and green) were visually detectable under ambient light. The same thin layers of dye on white paper were also visually detectable when they fluoresced under both short UV wavelength (254 nm) and long UV wavelength (365 nm), by visually examining the coated paper with a 4 watt UVGL-25 Compact UV Lamp, available from UVP of Upland, Calif.

TABLE 4

Components used for Examples 11-15.

| | Phase | Example 11 | Example 12 | Example 13 | Example 14 | Example 15 |
|---|---|---|---|---|---|---|
| IPM | oil | 43.43 g | 43.43 g | 43.43 g | 43.43 g | 43.43 g |
| PE-5 | oil | 8.57 g | 8.57 g | 0 g | 0 g | 0 g |
| IOA/SMA/M-90G (40/40/20) 35% in IPM* | oil | 0 g | 0 g | 8.57 g | 8.57 g | 8.57 g |
| Benzyl Alcohol | oil | 5 g | 5 g | 5 g | 5 g | 5 g |
| Span 80 | oil | 2 g | 2 g | 2 g | 2 g | 2 g |
| REACTINT Green | oil | 0 g | 0 g | 0.5 g | 0 g | 0.5 g |
| REACTINT Orange | oil | 0 g | 0 g | 0 g | 0.5 g | 0 g |
| Water | water | 39.3 g | 20.3 g | 19.8 g | 19.8 g | 38.8 g |
| SOFTCAT Sk-MH | water | 0.7 g | 0.7 g | 0.7 g | 0.7 g | 0.7 g |
| Lidocaine (HCl) | water | 1 g | 0 g | 0 g | 0 g | 1 g |
| 20% PHMB | water | 0 g | 20 g | 0 g | 20 g | 0 g |
| 20% CHG | water | 0 g | 0 g | 20 | 0 g | 0 g |

Example 16

Hydroalcoholic Composition Comprising a Polymeric Colorant and a Medicament The ingredients listed in Table 5 were combined as described below. The polymeric colorant PE-4 (described in Preparative Example 4) was added to the IPA and dissolved. The water was added to the mixture with stirring. The CHG solution was added to the mixture with stirring. The resulting mixture was shaken and stirred until uniform. The composition was highly colored. After spreading/painting a thin layer of the prepared dyes on white printer paper the dyes (yellow and green) were visually detectable under ambient light. The same thin layers of dye on white paper were also visually detectable when they fluoresced under both short UV wavelength (254 nm) and long UV wavelength (365 nm), by visually examining the coated paper with a 4 watt UVGL-25 Compact UV Lamp, available from UVP of Upland, Calif.

TABLE 5

Components used for Example 16.

| Component | Grams |
|---|---|
| PE-4 | 6 |
| IPA | 70 |
| PD-1 | 10 |
| Water | 10 |
| 20% CHG | 10 |

Reference Example 1

Preparation of a Malachite Green PEI Polymeric Dye and Demonstration of Color on Skin A 10% w/v solution of polyethylenimine (PEI) was prepared by adding 10 grams of water free PEI, (LUPASOL WF from BASF; Ludwigshafen, Del.) to 90 mL of water and pH adjusting to about 10 with hydrochloric acid. An amount of 10 mg of malachite green isothiocyanate (Invitrogen, Carlsbad, Calif.) was dissolved in 3 mL of dry dimethylformamide. Then, 3 mL of the 10% PEI solution were mixed in a vial with 100 μL of the malachite green isothiocyanate solution, protected from light by wrapping the vial in aluminum foil, and gently mixed for four hours at room temperature. The mixture was then placed in a dialysis unit (10,000 molecular weight cut off Slide-A-Lyzer dialysis cassette, Thermo Fisher Scientific, Pierce Protein Research Products, Rockford, Ill.) and dialyzed against about 500 mL of distilled water for approximately 4 hours. This was repeated two more times, dialyzing against a fresh 500 mL aliquot of distilled water each time, to remove any unreacted dye. The dialyzed polymeric dye was then brought to pH 6 with acetic acid and was found to be dark green in color. The polymeric dye was diluted 1:10 with water and painted onto very light colored pig skin. After drying for at least 10 minutes, a green area clearly was observed with the unaided eye.

Reference Example 2

Preparation of a LISSAMINE Rhodamine B PEI Polymeric Dye and Demonstration of Fluorescence on Skin An amount of 3 mL of the 10% w/v polyethylenimine (PEI) solution in dry dimethylformamide with about 1 mg of LISSAMINE rhodamine sulfonyl chloride (Invitrogen, Eugene, Oreg.) in a sealed vial and gently mixed overnight protected from light by wrapping in aluminum foil. The prepared LISSAMINE rhodamine B 10% PEI solution was dialyzed against about 500 mL of distilled water for about four hours. This was repeated twice with fresh water to remove any unreacted LISSAMINE rhodamine dye. This polymeric dye solution, which was a light yellow in color was painted onto very light colored pig skin. The composition on the pig skin was barely visible to the unaided eye under ambient lighting, but its fluorescence was clearly observed when it was illuminated using a long wavelength UV light (Cole-Parmer, Vernon Hills, Ill.).

Reference Example 3

Preparation of a Hydroalcoholic LISSAMINE Rhodamine B PEI Polymeric Dye and Demonstration of Fluorescence on Skin An alcohol based solution of the prepared polymeric dye was prepared by mixing 1 mL of the dialyzed aqueous LISSAMINE rhodamine B PEI solution (from Reference Example 2) with 2.5 mL of isopropanol. This alcohol-based preparation of the LISSAMINE rhodamine B PEI polymeric dye was painted on the pig skin and allowed to dry. As with the aqueous solution of Preparative Example 2, the polymeric dye was barely visible to the unaided eye under ambient lighting, but its fluorescence clearly was visible when the composition was illuminated with the long wavelength UV light.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A composition, comprising:
   at least one polymeric colorant comprising a polymer component with at least one colorant component covalently bound thereto;
   a medicament; and
   a liquid vehicle comprising a lower alcohol and water;
   wherein the at least one colorant component does not react directly or indirectly with the medicament;
   wherein the at least one polymeric colorant is soluble in the composition, and
   wherein the at least one polymeric colorant is cationic, nonionic, or zwitterionic.

2. A composition, comprising:
   a first polymeric colorant comprising a first polymer component with a first colorant component bound thereto;

a second polymeric colorant comprising a second polymer component with a second colorant component covalently bound thereto;
a medicament; and
a liquid vehicle comprising a lower alcohol and water;
wherein each of the first and second colorant components does not react directly or indirectly with the medicament; wherein at least one polymeric colorant is cationic, nonionic, or zwitterionic and
wherein at least one polymeric colorant is soluble in the composition.

3. The composition of claim 1, wherein at least one colorant component comprises one or more chromophore and/or one or more fluorophore.

4. The composition of claim 1, wherein at least one polymer component is derived from vinyl monomers.

5. The composition of claim 1, wherein at least one polymer component comprises a condensation polymer.

6. The composition of claim 1, wherein at least one polymer component comprises a polyamine or a polyamide.

7. The composition of claim 1, wherein the polymer component comprises a natural polymer selected from the group consisting of a polysaccharide and a polypeptide.

8. The composition of claim 1, wherein the polymer component comprises a synthetic polymer selected from the group consisting of a polyethyleneimine polymer, a polyurethane polymer, a polyether polymer, and a polyacrylate polymer.

9. The composition of claim 1, wherein at least one polymeric colorant comprises a film-forming polymeric colorant.

10. The composition of claim 7, wherein the film-forming polymeric colorant is capable of forming a self-supporting film with a dry thickness of 40-50 microns.

11. The composition of claim 1, further comprising a film-forming polymer.

12. The composition of claim 1, wherein at least one colorant component comprises a dye selected from the group consisting of a phthalocyanine dye, an acid dye, a basic dye, an azo dye, an anthroquinone dye, a xanthene dye, a triphenylmethane dye, a reactive dye, a direct dye, a vat dye, a sulfur dye, a disperse dye, a mordant dye, and a fluorescent dye.

13. The composition of claim 1, wherein the medicament is selected from the group consisting of an antimicrobial agent, an antiseptic, an antibiotic, an analgesic, an enzyme, and a mixture of any of two or more of the foregoing medicaments.

14. The composition of claim 13, wherein the medicament comprises an antimicrobial agent; wherein, when the composition is contacted for a period of time with an area of a surface having a number of cultivable microorganisms present thereon, the concentration of antimicrobial compound in the liquid vehicle is sufficient to reduce the number of cultivable microorganisms on the area of the surface.

15. The composition of claim 14, wherein the antimicrobial agent comprises a chemical antiseptic compound.

16. A method of preparing skin as a site for a surgical procedure, comprising:
providing a composition that includes at least one polymeric colorant comprising a polymer component with a colorant component covalently bound thereto, an antimicrobial agent, and a liquid vehicle comprising a lower alcohol and water;
wherein the antimicrobial agent is present at a sufficient concentration in the composition such that, when a predetermined quantity of the composition is contacted with a predetermined area of skin having a number of cultivable microorganisms present thereon; the antimicrobial agent is capable of reducing the number of cultivable microorganisms;
wherein the colorant component does not react directly or indirectly with the antimicrobial agent;
wherein the at least one polymeric colorant is soluble in the composition; wherein the at least one polymeric colorant is cationic, nonionic, or zwitterionic;
applying the composition to an area of skin selected for the surgical procedure; and
verifying the area to which the composition was applied by observing on the skin a color associated with the composition.

17. A method of killing microorganisms on mammalian skin prior to a percutaneous procedure comprising:
providing a composition that includes at least one polymeric colorant comprising a polymer component with a colorant component covalently bound thereto, an antimicrobial, and a liquid vehicle comprising a lower alcohol and water;
wherein the antimicrobial is present in a concentration of at least 0.25% wt/wt of the composition;
wherein the colorant component does not react directly or indirectly with the antimicrobial;
wherein the at least one polymeric colorant is soluble in the composition; wherein the at least one polymeric colorant is cationic, nonionic, or zwitterionic;
applying the composition to an area of mammalian skin;
wherein applying the composition to the area reduces the number of cultivable microorganisms on the mammalian skin; and
verifying, by human eye, the area to which the composition was applied by observing on the area a color associated with the composition.

18. The composition of claim 1, wherein the composition comprises less than 10% volatile organic solvent.

19. The composition of claim 1, wherein composition is an emulsion.

20. The composition of claim 1, further comprising a surfactant.

21. The composition of claim 1, wherein the polymeric colorant is cationic or nonionic.

22. The composition of claim 21, wherein the medicament is cationic.

* * * * *

UNITED STATES PATENT AND TRADEMARK OFFICE
CERTIFICATE OF CORRECTION

| | | |
|---|---|---|
| PATENT NO. | : 9,717,798 B2 | Page 1 of 2 |
| APPLICATION NO. | : 14/358817 | |
| DATED | : August 1, 2017 | |
| INVENTOR(S) | : Louis Haddad et al. | |

It is certified that error appears in the above-identified patent and that said Letters Patent is hereby corrected as shown below:

In the Specification

Column 4
Line 40, Delete "and or" and insert -- and/or --, therefor.

Column 7
Line 55, Delete "octinedine," and insert -- octenidine, --, therefor.

Column 9
Line 15, Delete "anthroquinone" and insert -- anthraquinone --, therefor.
Line 46, Delete "and or" and insert -- and/or --, therefor.

Column 14
Line 43, Delete "priolocane," and insert -- prilocaine, --, therefor.

Column 15
Line 55, Delete "octenidene," and insert -- octenidine, --, therefor.
Line 56, Delete "pyridium" and insert -- pyridinium --, therefor.

Column 16
Line 3, Delete "trymethoprim," and insert -- trimethoprim, --, therefor.
Line 8, Delete "coxacillin," and insert -- cloxacillin, --, therefor.
Line 29, Delete "domeclocycline," and insert -- demeclocycline, --, therefor.
Line 33, Delete "carbaphenern," and insert -- carbapenem, --, therefor.
Line 45, Delete "carbaphenern," and insert -- carbapenem, --, therefor.
Line 46, Delete "oxacephem," and insert -- oxazepam, --, therefor.
Line 52, Delete "azino-micyin-A," and insert -- azino-mycin-A, --, therefor.
Line 53, Delete "calichemycin," and insert -- calicheamicin, --, therefor.
Lines 58-59, Delete "mitoxantorone," and insert -- mitoxantrone, --, therefor.
Line 65, Delete "narbofloxacin," and insert -- marbofloxacin, --, therefor.

Signed and Sealed this
Twenty-seventh Day of February, 2018

Andrei Iancu
*Director of the United States Patent and Trademark Office*

CERTIFICATE OF CORRECTION (continued)
U.S. Pat. No. 9,717,798 B2

Column 21
Line 7, Delete "roseacea," and insert -- rosacea, --, therefor.

Column 23
Line 11, Delete "anthroquinone" and insert -- anthraquinone --, therefor.

Column 26
Line 56 (Approx.), Delete "Spartanberg, SC" and insert -- Spartanburg, SC --, therefor.

Column 29
Line 40, Delete "60 C." and insert -- 60° C. --, therefor.

In the Claims

Column 33
Line 40, In Claim 12, delete "anthroquinone" and insert -- anthraquinone --, therefor.

Column 34
Line 14 (Approx.), In Claim 16, delete "thereon;" and insert -- thereon, --, therefor.